United States Patent [19]

Yarger

[11] Patent Number: 4,867,747
[45] Date of Patent: Sep. 19, 1989

[54] SURGICAL ASPIRATOR SLEEVE

[76] Inventor: Richard J. Yarger, 4908 Douglas Dr., Yakima, Wash. 98908

[21] Appl. No.: 300,748

[22] Filed: Jan. 19, 1989

Related U.S. Application Data

[63] Continuation of Ser. No. 28,788, Mar. 23, 1987, abandoned.

[51] Int. Cl.[4] .......................................... A61M 5/325
[52] U.S. Cl. ...................................... 604/263; 128/4; 604/902
[58] Field of Search ...................... 604/263, 266–269, 604/902, 119, 192–198; 128/4; 433/91, 96; 138/108, 119, 121

[56] References Cited

U.S. PATENT DOCUMENTS

| | | | |
|---|---|---|---|
| 1,557,744 | 10/1925 | Tobriner | 433/91 |
| 2,255,657 | 9/1941 | Freedman | 128/23 |
| 2,504,557 | 4/1950 | Lumian | 433/96 |
| 2,529,499 | 11/1950 | Jankelson | 433/96 |
| 3,084,440 | 4/1963 | Wenof | 433/96 |
| 3,240,233 | 3/1966 | Johnston | 138/108 |
| 3,314,430 | 4/1967 | Alley et al. | 604/268 |
| 3,333,340 | 8/1967 | Boisvert | 433/91 |
| 3,528,427 | 9/1970 | Sheridan | 604/268 |
| 3,937,220 | 2/1976 | Coyne | 604/119 |
| 4,022,218 | 5/1977 | Riddick | 604/902 |
| 4,068,664 | 1/1978 | Sharp et al. | 604/268 |
| 4,074,435 | 2/1978 | Orsing | 433/96 |
| 4,182,343 | 1/1980 | Inaba | 604/268 |
| 4,265,621 | 5/1981 | McVey | 433/91 |
| 4,767,404 | 8/1988 | Renton | 604/902 |

Primary Examiner—Jerome L. Kruter
Attorney, Agent, or Firm—Christensen, O'Connor, Johnson & Kindness

[57] ABSTRACT

A cylindrical sleeve, having one closed end, to be releasably positioned about the tip portion of a surgical aspirator to aid in preventing clogging. The sleeve is formed of resiliently deformable material that defines plural spaced orifices and ribs on both interior and exterior surfaces to allow entry of fluid and small debris to the aspirator therein but aid in preventing the entry of tissue or larger debris that causes clogging or plugging. The ribs and additional fenstrae maintain aspirator action and prevent its discontinuance by non-dissected tissue's blocking of sleeve orifices.

7 Claims, 2 Drawing Sheets

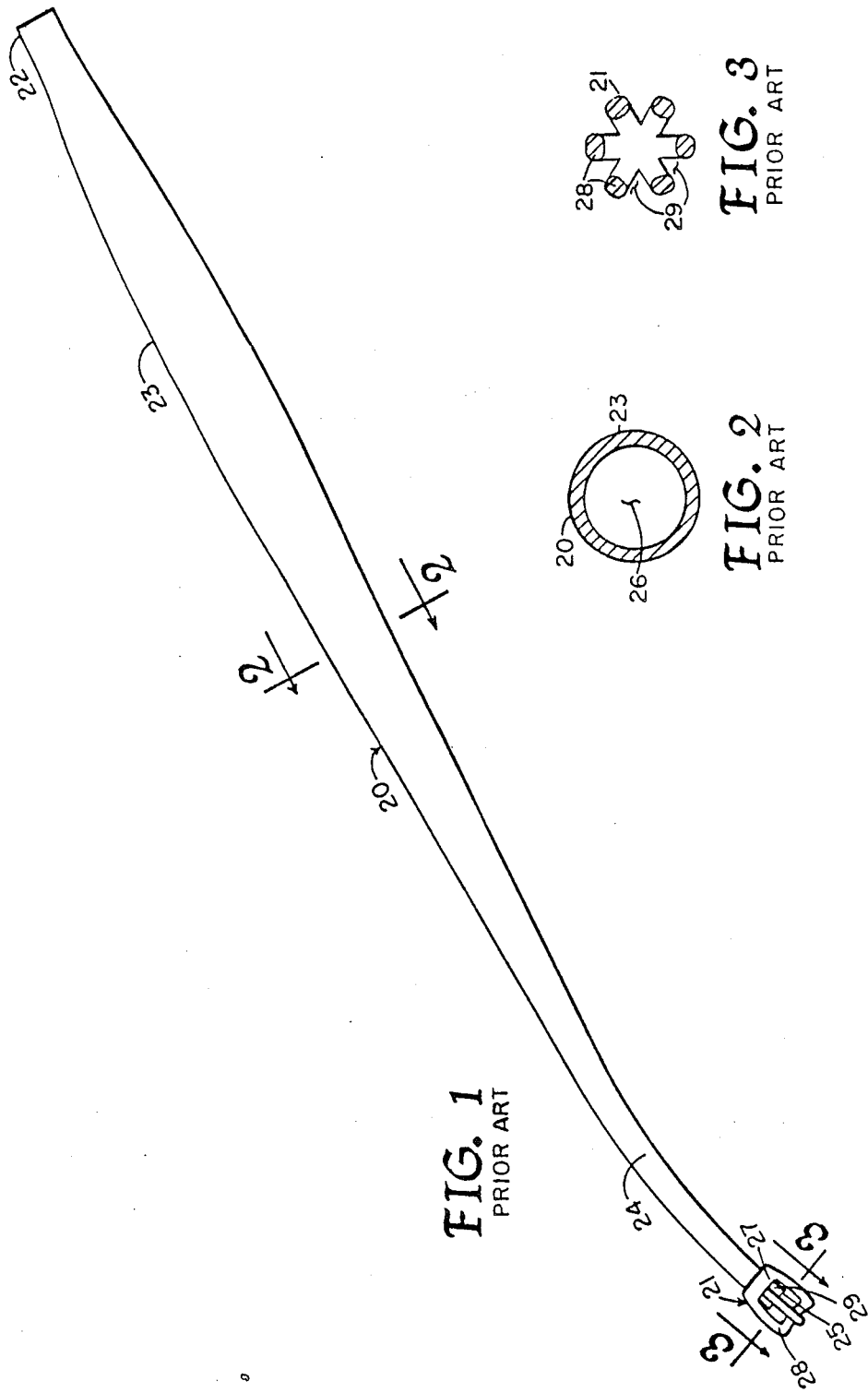

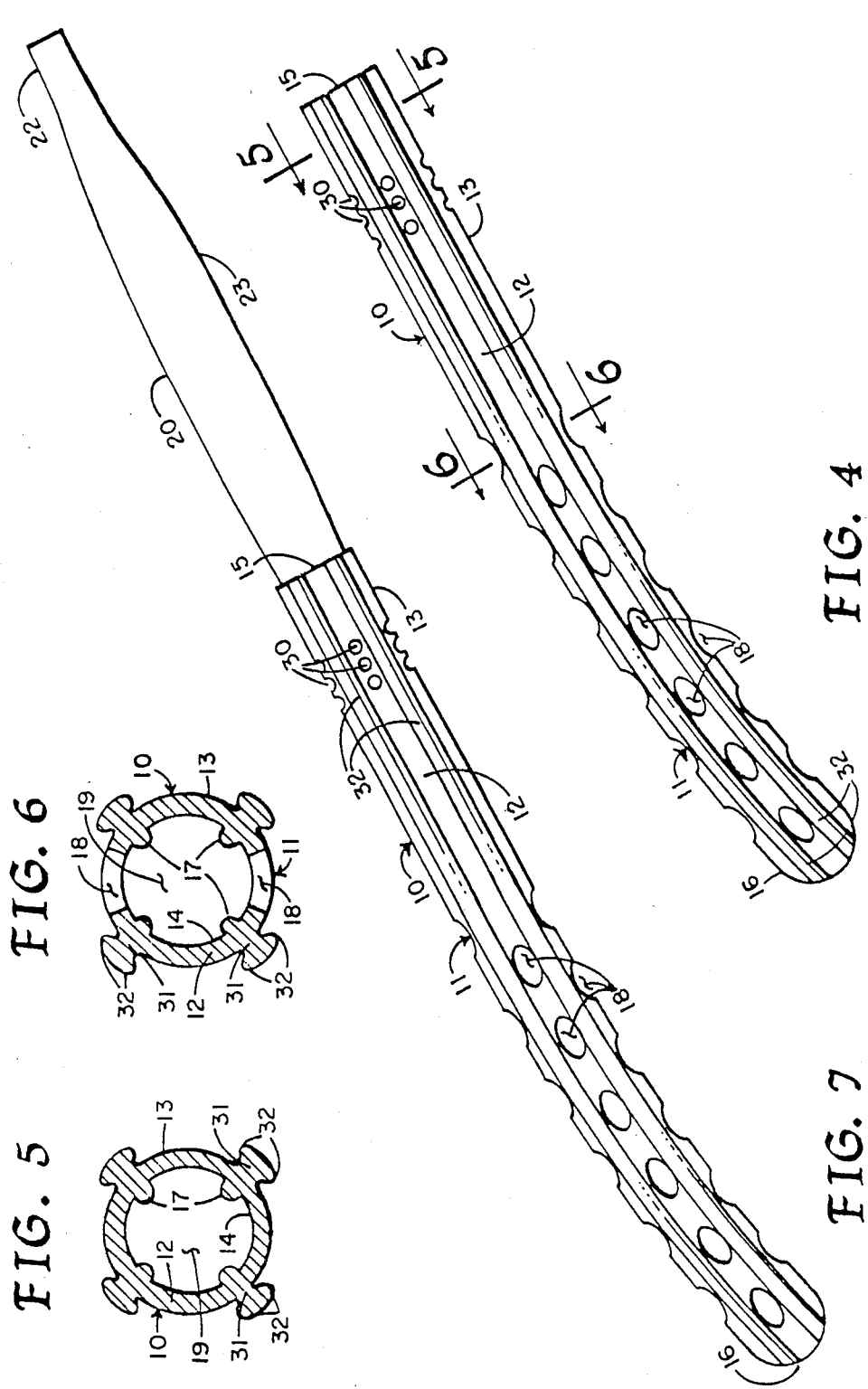

SURGICAL ASPIRATOR SLEEVE

BACKGROUND OF INVENTION

This application is a continuation of application based on prior copending application Ser. No. 028,788, filed on Mar. 23, 1987, now abandoned.

1. Prior Applications

There are no applications related hereto heretofore filed in this or any foreign country.

2. Field of Invention

This invention relates generally to surgical aspirators and more particularly to a releasable sleeve for the tip portion of such aspirators that tends to prevent clogging during use.

BACKGROUND OF INVENTION

Whenever parts of a body are surgically invaded the trauma involved tends to cause the accumulation of body fluids from the tissue itself or from various body fluid systems. The surgical invasion itself normally also creates debris of various sorts, and particularly severed portions of tissue and irrigation fluids, which normally must be removed from the surgical site. Aspirators of many and various types have heretofore become known to remove this material.

In their early history, aspirators generally were formed of elongate metal tubes with a smaller input orifice at a first end and a larger connector orifice at the second end to releasably communicate with an aspirator system providing a waste reservoir and source of vacuum. In use such aspirators were found neither particularly convenient nor reliable as they commonly plugged either from disconnected tissue or other debris in the surgical site or from tissue in place with which they came into contact. With such devices, if the vacuum produced by an aspirator system were too strong, the tip might even damage tissue in place which it contacted, making us not only inconvenient but also requiring that the apparatus be operated with substantial care.

As time progressed and these problems were more fully realized, various solutions were presented, commonly in the form of some sort of a guard about the tip or input portion of the aspirator tube. As the tip guard evolved, the straight cylindrical form of the aspirator tube changed to assume a more curvilinear configuration with a medial bulbous enlargement, that served both as a handle structure and a vacuum reservoir, and with a diametrically smaller and generally tapering input portion that was curved, especially near its tip, for easier manipulation and use. A typical aspirator of this type as commonly used in modern day surgery is illustrated in FIG. 1 of the drawings associated herewith. In general in the present day such aspirators are designed for single use and are commonly formed of polymeric material because of its transparency and low cost.

Tip guards are commonly used with such aspirator tubes but such guards have not become particularly standardized and heretofore have taken many and various forms. All such tip guards, however, have generally had the same essential characteristics of being quite small in both axial and radial dimension, being irreleasably positionable on or in the immediate vicinity of the tip, and having a plurality of orifices defined therein so that if one orifice plugs others may remain operative. By reason of these characteristics, the guarded aspirator tip is more functional than an unguarded tip, but it is not too much better, as the guarded tip still tends to plug and clog.

Orifices defined in tip guards generally are of a size as large or larger than the associated aspirator tip orifice, so if tissue or debris be presented to them it may commonly pass therethrough to plug the input orifice of the aspirator tube. More importantly when an aspirator with this type of tip guard be used in a surgical site adjacent a surface of soft tissue that tissue may move and be deformed, both by the manipulation of the aspirator and by its vacuum, so that commonly such tissue may plug all of the orifices defined in an aspirator guard. This tendency is roughly proportionable to the external size of the tip guard.

The instant invention seeks to prevent such plugging by providing an auxiliary closed-end sleeve to fit about both aspirator and tip guard. My sleeve takes the configuration of a cylindrical tube and is formed of resiliently deformable material so that it will deform to accommodate the curvilinear shape of the tip of present day aspirators. The tube defines plural, spaced, relatively small orifices over a substantial portion of is area and is dimensioned so that it may be positionally maintained by frictional engagement on the aspirator tube. The peripheral surface of the sleeve, wherein orifices are defined, is of substantially greater area than are the peripheral surfaces of tip guards heretofore commonly used on surgical aspirators, differing normally by a factor of fifty or more. Elongate axially aligned ribs are provided on the external surface of my guard to further aid in preventing clogging of orifices, especially as by tissue in place surrounding a surgical site. With such size and configuration it becomes quite unlikely that all of the orifices in the sleeve may be plugged at one time, either by debris at the surgical site or by adjacent soft tissue. My sleeve is especially useful in the gross cleaning of surgical sites and for use in larger sites. If a smaller working area be required than is allowed by my sleeve, the sleeve may readily be removed and either the aspirator tube with tip guard, or if necessary without tip guard, used independently.

My sleeve also, when used in association with a tip guard, provides a double orifice system through which any matter must pass before it might arrive at an aspirator tube tip to plug that tip and obviously the probability of such debris passing through both orifice systems is less then the probability of its passing through only one. This action is further enhanced by internal ribs defined on the interior surface of my sleeve which maintain it at a spaced distance outwardly from the periphery of an associated aspirator tube. This structure provides auxiliary orifices for the entry of air at the junction of the inner end of my sleeve with an aspirator tube to make it very nearly impossible to plug all of the sleeve's orifices at one time under any conditions, and also requires that there will always be space between the aspirator and my sleeve wherein fluids may collect and debris may remain without moving to or through either the tip guard or aspirator tube tip.

My invention resides not in any one of these structural features per se, but rather in the synergistic combination of all of them to provide the functions necessarily flowing therefrom to distinguish my invention from the prior art.

BRIEF DESCRIPTION OF INVENTION

My invention generally provides an elongate cylindrical sleeve having an open end and for aspirator tube insertion and an enclosed tip end. The tip portion of the sleeve, over at least half of the sleeve length, defines plural spaced orifices. The inner surface of the sleeve defines a channel to fit over and about the guard and tip portion of an aspirator tube to be serviced and yet is small enough to frictionally maintain the rearward portion of the sleeve on the aspirator tube. Both inner and outer surfaces of the sleeve define plural, radially spaced, axially extending ridges. The sleeve is formed of resiliently deformable material to allow its conformation to a curvilinear shape of an aspirator tube.

In providing such a device it is:

A principal object of my invention to create a sleeve for surgical aspirator tubes having a tip guard that allows the normal functioning of the aspirator but aids in preventing its clogging from either debris or soft tissue adjacent a surgical site.

A further object of my invention to provide such a sleeve that has ribbed inner and outer surfaces to maintain the sleeve at a spaced distance from the aspirator to be serviced and from soft tissue defining a surgical site, to aid in preventing the blocking of either sleeve or aspirator orifices.

A further object of my invention to provide such a device that has relatively small spaced orifices defined over a substantial part of both the tip and inner portion of its surface to make unlikely the possibility that all orifices may be simultaneously plugged.

A still further object of my invention to provide such a sleeve that is formed of resiliently deformable material, such as a transparent polymer, that may conform to the curvilinear shape of a particular aspirator tube and allow viewing of that tube.

A still further object of my invention to provide such a sleeve that is of new and novel design, of rugged and durable nature, of simple and economic manufacture and one otherwise well adapted to the uses and purposes for which it is intended.

DESCRIPTION OF DRAWINGS

In the accompanying drawings which form a part hereof and wherein like numbers of reference refer to similar parts throughout:

FIG. 1 is an orthographic surface view of a typical curvilinear aspirator tube and tip guard heretofore known in the prior art and commonly used in the modern day surgical practice.

FIG. 2 is a somewhat enlarged transverse cross-sectional view through the medial portion of the aspirator tube of FIG. 1, taken on the line 2—2 thereon in the direction indicated by the arrows.

FIG. 3 is a somewhat enlarged transverse cross-sectional view through the tip guard structure of the aspirator tube of FIG. 1, taken on the line 3—3 thereon in the direction indicated by the arrows.

FIG. 4 is an orthographic side view of the sleeve of my invention showing its various parts, their configuration, and relationship.

FIG. 5 is a somewhat enlarged transverse cross-sectional view through the open end portion of the sleeve of FIG. 4, taken on the line 5—5 thereon in the direction indicated by the arrows.

FIG. 6 is a somewhat enlarged transverse cross-sectional view through the orifice structure of the sleeve of >FIG. 4, taken on the line 6—6 thereon in the direction indicated by the arrows.

FIG. 7 is an orthographic side view of the sleeve of my invention in operative position on a prior art aspirator tube and guard such as illustrated in FIG. 1.

DESCRIPTION OF THE PREFERRED EMBODIMENT

My invention generally provides sleeve body 10 defining orifices 11.

Body 10 provides cylindrical tube 12 having outer peripheral surface 13 and inner peripheral surface 14 with open aspirator end 15 and enclosed tip 16. The tip is preferably configured substantially as a hemisphere, as illustrated, to provide no sharp edges or corners that might either be physically damaged or might themselves physically damage soft tissues surrounding a surgical site.

Inner surface 14 of body 12 defines plural, elongate, axially extending, inwardly projecting positioning ribs 17, four in the instance illustrated, arrayed with circular symmetry about the inner surface of the body. The number, arrangement, and positioning of these ribs is not particularly critical, though generally it is more convenient if they be at least three in number so arrayed as not to coincide with orifices defined in the tip portion of the body.

Outer surface 13 of the body defines plural spacing ribs 31 again axially aligned and projecting radially outwardly a spaced distance from the body. Generally inner and outer ribs are radially aligned with each other in cooperating pairs to position them between orifices or fenstrate. The radially outer parts of the outer ribs may provide somewhat bulbously enlarged portions 32 to aid in spacing the body from tissue defining a surgical site, though this feature, if used, may make the formation process more difficult.

The body of my invention is formed of some semi-rigid, resiliently deformable material that is adaptable for use in the medical arts. 1 prefer a polymeric or resinous plastic material such as is commonly used in surgical apparatus in the present day. With the economics of modern medical practice, the sleeve will normally be provided for one time use in a sterilized container. This, of course, is not necessary to my invention and obviously materials that may be sterilized between uses may be provided. In general though, in general sterilization and recycling for reuse may cost more than the initial cost of the product. My sleeve may be formed by various of the manufacturing processes used for such purposes in the present day. A length of continuous extruded tubing of appropriate cross-section may be cut to appropriate length, with the tip being closed by deformation and joinder. The structure might also be formed by injection molding if this type of formation process be desired.

Positioning ribs 17 preferably, but not necessarily, are formed with rounded inward projections so that a smaller surface area might contact an aspirator tube to be serviced to allow easy placement and removal of my sleeve. Often if any substantial area of a sleeve be in direct frictional contact with an aspirator tube the two may generate substantial frictional forces and be fairly difficult to move relative to each other.

Orifice structure 11 of my sleeve includes a plurality of spaced holes 18 defined through the walls of body 12. These holes in the instance shown are shaped in the form of ellipses. This shape obviously is not necessary but provides an orifice of greater area but lesser dimension in one direction which oftentimes may prohibit the passage of elongate particles that could pass through the orifice except for their orientation relative thereto. There is no required number, size or array of these orifices but the configuration illustrated has been found empirically to be quite functional. As illustrated, holes 18 are arrayed in four axially parallel lines and in the case of ellipses are oriented with longer axes along an axially extending line with spacing substantially a hole length apart. The holes in adjacent lines are so related that they would be staggered relative to each other. The size of the holes is preferably such that the holes may be arrayed between adjacent positioning and spacing ribs defined on the surfaces of body 12. Normally these holes are formed in resiliently flexible plastic by punching with a die aided by an internal arbor, but they may be formed by other of the processes presently known in the plastic manufacturing arts.

Additional orifices or fenstrae 30 may be defined immediately inwardly adjacent aspirator end 15 of the body to assure airflow through the sleeve if other orifices should become plugged. These fenstrae are not essential to my sleeve but do provide more absolute assurance of operability.

The configuration and sizing of my sleeve is somewhat critical. Tubular chamber 19 defined by tubular body 12 should be somewhat larger than the tip portion of an aspirator tube to be serviced but yet should not be larger than the medial bulbous portion of that aspirator tube upon which my tube is to be positioned so that the tube may be frictionally maintained in its rearward or inner part. Normally this will require a plastic tubing of approximately one-half inch external diameter depending upon aspirator size, sleeve tube thickness and depth of inward projection of the positioning ridges. It is not necessary, and in fact not desirable, that the tip guard of an aspirator tube to be serviced extend completely to the end of my sleeve. It is preferable that the tip guard be a spaced distance from a sleeve tip so that the tip portion of the sleeve may tend to form somewhat of a reservoir for collection of fluids to be aspirated The sizing of the aspirator tube in FIG. 1 and of the sleeve in FIG. 4 are approximately at full scale.

Having thusly described the structure of my invention, its operation may be understood.

The type of aspirator tube 20 and tip guard 21 with which my invention is particularly designed to function is illustrated in FIG. 1. Aspirator tube 20 in general provides a tubular structure of circular cross-section having smaller connecting portion 22 in its rearward part communicating with medial, larger bulbous portion 23, which forms a handle and reservoir to stabilize vacuum in the device, which in turn communicates with forwardly tapering and curved neck portion 24 which terminates in aspiration orifice 25. The thickness of the wall defining aspirator tube 20 is relatively uniform throughout so that chamber 26 defined therein is of shape slightly smaller but substantially similar to that of the external periphery.

Tip guard 21 provides connector ring 27 sized and configured to fastenably engage the outer surface of the aspirator tube immediately inwardly of orifice 25. The connector ring structurally communicates with and supports tip structure 28 defining plural orifices 29 for the passage of material to be aspirated. The tip structure normally is relatively small and generally of a diameter somewhat less than the largest diameter of an associated aspirator tube. The form of aspirator tube and tip guard illustrated is well known and commonly used in modern day surgical arts.

To use my sleeve a device is formed, according to the foregoing specifications, to the configuration illustrated in FIG. 4. Tip guard 21 of an aspirator to be serviced is inserted through inner open end 15 of sleeve body 12 and the sleeve thereafter manually moved upon the aspirator tube until its inner aspirator end becomes frictionally engaged with the tip facing portion of bulbous enlargement 23. As the sleeve moves upon the curved tip portion of the aspirator, it will assume generally the same curvilinear shape of the aspirator tube by reason of its resilient nature and intermitting relationship with the aspirator tube. Normally tip guard 21 of an aspirator tube to be serviced will be of a size appropriate to fit within channel 19 defined by my sleeve, and, if so, the tip guard should be left in place on an aspirator tube when used with my invention. If a tip guard is too large to fit within a sleeve cavity, the guard may be removed. Some tip guards are releasably maintained on aspirator tubes and, if this be the case with a particular tip guard, it may be manually removed; if this not be the case, the tip guard may be mechanically severed at its inner end for removal.

When my sleeve is positioned on an aspirator tube as aforesaid, it is to be noted that the inner or aspirator end 5 of the sleeve will contact the aspirator tube by means of the inner portions of positioning ridges 17, so that there will be orifices defined between my sleeve, the aspirator tube, and each of the positioning ridges. By reason of the general operation of the device and the position of these orifices they almost always will be in a position where they are not and cannot be simultaneously blocked, so that if all of the other orifices defined in the sleeve become plugged or blocked the aspirator will still draw air from the ambient atmosphere through the orifices between the tube and the aspirator end of my sleeve.

Once my sleeve is established on an aspirator tube, the combination is used substantially in the same manner as an ordinary aspirator tube without the sleeve. The forward portion of the device is placed in the lower portion of a surgical site and various fluids and debris therein will tend to pass through holes 18 in the forward portion of the sleeve to tip orifice 25 of the aspirator tube being serviced from whence they are exhausted through the aspirator in the ordinary fashion. Depending upon the manner of manipulation of an aspirator using my sleeve, the tip portion of the sleeve may serve as a reservoir for the collection of material to be aspirated, especially as when the tube assumes a somewhat vertical position with tip lowermost. Should orifices of my sleeve become plugged or should the aspirator become plugged, my sleeve may be readily removed, if necessary, by manual manipulation, in reverse of the manner in which it was established, to allow cleaning of its chamber and any of the orifices.

It is to be noted from the foregoing description that although my aspirator sleeve is described as being a separate structure, releasably positionable upon an aspirator tube, it might be formed integrally with an aspirator tube in the process of manufacture and that compound structure too would be within the ambit of my invention.

It is further to be noted that my sleeve could be used as an aspirator tube per se if it be interconnected with some source of vacuum at its inner or open aspirator end. This, however, is not its primary purpose and with its multiple orifice structure distributed over a relatively large area, its operation as an aspirator tube per se would be rather gross and not too finely regulatable, ii in fact ordinary aspirator mechanism would support its operation.

The foregoing description of my invention is necessarily of a detailed nature so a specific embodiment might be set forth as required. It is to be understood, however, that various features and parts are susceptible of modification, multiplication, and rearrangement without departing from the spirit, essence or scope of my invention.

Having thusly described my invention, what I desire to protect by Letters Patent and

What I claim is:

1. A combination sleeve and surgical aspirator tube having a straight and a curved profile, the aspirator tubes having an enlarged medial portion, an elongate forward portion extending forwardly of the medial portion, a tip in the end of the forward portion opposite the medial portion and with no part of the forward portion being diametrically larger than the enlarged medial portion, said sleeve comprising:

an elongate, nominally straight tubular body defining an internal channel having an open, rearward aspirator end and an enclosed, forward tip end, said tubular body formed from resilient, deformable material over the forward portion of the surgical aspirator tube to receive the forward portion of the aspirator tube therein and to assume the curved profile of the forward portion of the aspirator tube means to secure said tubular body to an aspirator tube to prevent longitudinal movement of said tubular body;

wherein said body defining plural, spaced orifices at least in the forward tip portion, at a spaced distance rearwardly from the tip end, to communicate through the tubular body to allow passage of material to be aspirated into the internal channel defined by the tubular body; and, wherein the size of the internal channel of said tubular body is sufficiently larger than the exterior of the forward portion of the aspirator tube to enable the material passing into the channel through the orifices to flow through the internal channel between the interior of the tubular body and the exterior of the aspirator tube toward the forward tip of the aspirator tube.

2. The sleeve of claim 1, wherein the open, rearward end of the tubular body is resiliently expandable.

3. The sleeve of claim 1 further characterized by:

the inner surface of the sleeve defining plural inwardly projecting elements to positionally maintain the aspirator tube being serviced in a medial position within the channel defined by the sleeve.

4. The sleeve of claim 1 further characterized by:

the outer surface of the sleeve having plural outwardly projecting ribs to aid in spacing the orifices defined in the sleeve from tissue defining a surgical site.

5. A conversion sleeve for elongate aspirator tubes of both a straight and a curved profile, the aspirator tubes having a medial bulbous enlargement, an elongate forward section extending forwardly of the medial bulbous enlargement, a tip at the forward end of the forward section and with no portion of the forward section being diametrically larger than the medial bulbous enlargement, said conversion sleeve comprising:

an elongate, nominally straight, resiliently deformable, tubular body defining an internal channel to receive substantially the entire length of and to conform to the curvature of the elongate forward section of the aspirator tube, said body having an open rearward aspirator end an a forward enclosed tip end means to secure said tubular body to an aspirator tube to prevent longitudinal movement of said tubular body;

a plurality of spacedly arrayed orifices communicating through the tubular body, said orifices being spaced a distance from the enclosed tip end of the tubular body and including being located in the region of the body that overlaps the forward section of the aspirator tube;

a plurality of spaced, radially inwardly extending positioning ribs to maintain the aspirator tube substantially in a medial position in the internal channel; and, wherein the size of the internal channel of the tubular body is sufficiently larger than the exterior of the forward portion of the aspirator tube to allow the material to be aspirated that passes through the orifices and into the channel to flow through the internal channel between the interior of the tubular body and the exterior of the aspirator tube toward the forward tip of the aspirator tube.

6. The conversion sleeve of claim 5, wherein the open rearward end of said tubular body is resiliently expandable to snugly engage around the medial enlargement of the aspirator tube.

7. A conversion sleeve for elongate aspirator tubes of both straight and curved shapes, the aspirator tubes having a medial bulbous enlargement, a forward section extending forwardly of the medial bulbous enlargement, a tip at the forward end of the forward section and with no portion of the forward section being diametrically larger than the medial bulbous enlargement, said conversion sleeve comprising an elongate, resiliently deformable, tubular body defining an internal channel to accommodate the curvature of and releasably receive the forward section of the aspirator tube to be serviced, said body:

having an open rearward aspirator end and an enclosed tip end;

defining a plurality of spacedly arrayed orifices communicating therethrough, said orifices being spaced a distance from the enclosed tip end of the tubular body and being arrayed in radially spaced lines extending longitudinally of the tubular body;

a plurality of spaced, radially inwardly extending positioning ribs to maintain an aspirator tube substantially in a medial position in the internal channel;

wherein the outer surface of the sleeve body defining plural, spaced, radially outwardly extending spacing ribs; and, wherein the inner and outer spacing ribs being radially coincident and extending between the lines of spaced orifices.

* * * * *

UNITED STATES PATENT AND TRADEMARK OFFICE
CERTIFICATE OF CORRECTION

PATENT NO. : 4,867,747

DATED : September 19, 1989

INVENTOR(S) : Richard J. Yarger

It is certified that error appears in the above-identified patent and that said Letters Patent is hereby corrected as shown below:

Column 1, line 40, "us" should be --use--
Column 2, line 22, "is" should be --its--
Column 4, line 31, "fenstrate" should be --fenstrae--
Column 4, line 38, "1" should be --I--

Column 4, line 60, "tube" should be --tube,--

Column 6, line 13, "intermitting" should be --interfitting--
Column 6, line 27, "5" should be --15--
Column 7, line 3, "ii" should be --if--

Column 7, line 28, delete "to slidably engage" and insert --slide--.

Signed and Sealed this

Ninth Day of October, 1990

Attest:

HARRY F. MANBECK, JR.

*Attesting Officer*     *Commissioner of Patents and Trademarks*